US012685471B2

(12) United States Patent
Labyt et al.

(10) Patent No.: US 12,685,471 B2
(45) Date of Patent: Jul. 21, 2026

(54) SYSTEM FOR POSITIONING AND MAINTAINING THE POSITION OF A REFERENCE SENSOR AROUND A MAGNETOENCEPHALOGRAPHY HELMET

(71) Applicant: COMMISSARIAT A L'ENERGIE ATOMIQUE ET AUX ENERGIES ALTERNATIVES, Paris (FR)

(72) Inventors: Etienne Labyt, Grenoble Cedex (FR); William Fourcault, Grenoble Cedex (FR); Ilea Paquin-Honore, Lille (FR); Guilhem Laffont, Lille (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 21 days.

(21) Appl. No.: 18/547,735

(22) PCT Filed: Feb. 17, 2022

(86) PCT No.: PCT/EP2022/053901
§ 371 (c)(1),
(2) Date: Aug. 24, 2023

(87) PCT Pub. No.: WO2022/179925
PCT Pub. Date: Sep. 1, 2022

(65) Prior Publication Data
US 2024/0122514 A1     Apr. 18, 2024

(30) Foreign Application Priority Data
Feb. 25, 2021     (FR) ........................................ 2101839

(51) Int. Cl.
A61B 5/245     (2021.01)
A61B 5/00      (2006.01)
A61B 90/00     (2016.01)

(52) U.S. Cl.
CPC ............ *A61B 5/245* (2021.01); *A61B 5/6803* (2013.01); *A61B 90/08* (2016.02); *A61B 2560/0406* (2013.01); *A61B 2560/0462* (2013.01)

(58) Field of Classification Search
CPC .............................. A61B 5/245; A61B 5/6803
See application file for complete search history.

(56) References Cited

U.S. PATENT DOCUMENTS 3,990,757 A * 11/1976 Gill ...................... A62B 18/084
                                                      439/259
2005/0107716 A1* 5/2005 Eaton ................... A61B 5/0073
                                                      128/903
(Continued)

FOREIGN PATENT DOCUMENTS

CN     105147289 B     1/2018
CN     210203501 U     3/2020
(Continued)

OTHER PUBLICATIONS

OCR of WO 2010017641 A1 (Year: 2010).*
(Continued)

*Primary Examiner* — Christopher Koharski
*Assistant Examiner* — Helene Bor
(74) *Attorney, Agent, or Firm* — Oblon, McClelland, Maier & Neustadt, L.L.P.

(57) ABSTRACT

A system for positioning and maintaining a position of a reference sensor around a magnetoencephalography helmet. The system includes an arch comprising at least one fixing
(Continued)

branch for fixing the arch to an MEG helmet, a support plate on which the branch is fixed, a sensor support post fixed to the support plate of the arch; and a locking component for fixing the reference sensor to the post in at least one position defining the position with respect to an MEG helmet.

10 Claims, 5 Drawing Sheets

(56) References Cited

U.S. PATENT DOCUMENTS

| | | | |
|---|---|---|---|
| 2007/0106170 A1* | 5/2007 | Dunseath | A61B 5/291 |
| | | | 600/383 |
| 2008/0171930 A1* | 7/2008 | Abolfathi | A61B 90/11 |
| | | | 606/1 |
| 2017/0367650 A1* | 12/2017 | Wallois | G06F 3/015 |
| 2020/0315482 A1 | 10/2020 | Osaka et al. | |
| 2021/0011094 A1* | 1/2021 | Bednarke | A61B 5/6814 |
| 2022/0193456 A1* | 6/2022 | Thyagarajan | A61N 7/00 |
| 2022/0313133 A1* | 10/2022 | Gormley | G01R 33/032 |
| 2023/0218218 A1* | 7/2023 | Nenonen | A61B 5/245 |
| | | | 600/409 |
| 2025/0169712 A1* | 5/2025 | Shah | A61B 5/062 |

FOREIGN PATENT DOCUMENTS

| | | |
|---|---|---|
| CN | 110742607 B | 10/2020 |
| JP | 2020-151023 A | 9/2020 |
| WO | WO-2010017641 A1 * | 2/2010 ............ A61B 90/11 |
| WO | WO 2020/084194 A1 | 4/2020 |

OTHER PUBLICATIONS

TechTarget Contributor. (Sep. 3, 2014). Definition active sensor. What is active sensor? | Definition from TechTarget. https://www.techtarget.com/iotagenda/definition/active-sensor (Year: 2014).*

French Preliminary Search Report & Written Opinion Issued Oct. 15, 2021 in French Patent Application No. 21 01839 (with English Translation of Categories of Cited Documents), 9 pages.

International Search Report issued Apr. 29, 2022 in PCT/EP2022/053901 (with English Translation of Categories of Cited Documents & Written Opinion), 10 pages.

Boto et al., "Moving magnetoencephalography towards real-world applications with a wearable system", Nature, 555 (7698), Mar. 29, 2018, 27 pages, https://doi:10.1038/nature26147.

Hill et al., "Multi-channel whole-head OPM-MEG: Helmet design and a comparison with a conventional system", NeuroImage 219, May 29, 2020, 116995, pp. 1-20, https://doi.org/10.1016/l.neuroimage.2020.116995.

Borna et al., "Non-Invasive Functional-Brain-Imaging with an OPM-based Magnetoencephalography System", PLoS One 15 (1): e0227684, Jan. 24, 2020, pp. 1-24, https://doi.org/10.1371/journal.pone.0227684.

Fife et al., "Synthetic Gradiometer Systems for MEG", IEEE Transactions on Applied Superconductivity, vol. 9, No. 2, Jun. 1999, pp. 4063-4068.

* cited by examiner

SYSTEM FOR POSITIONING AND MAINTAINING THE POSITION OF A REFERENCE SENSOR AROUND A MAGNETOENCEPHALOGRAPHY HELMET

CROSS-REFERENCE TO RELATED APPLICATIONS

The present application claims priority to PCT Application No. PCT/EP2022/053901, filed Feb. 17, 2022, and French Application No. FR 2101839, filed Feb. 25, 2021. The contents of the above-identified applications are incorporated herein by reference.

TECHNICAL FIELD

The present invention relates to the general field of magnetoencephalography (MEG).

It deals more particularly with the fixing of a reference sensor to an MEG helmet.

Although described with reference to an application in which the MEG device is a helmet, the MEG device can be a magnetocardiography thoracic belt or a magnetoencephalography or fetal magnetocardiography abdominopelvic belt.

PRIOR ART

Optical pumping magnetometers (OPM) are beginning to be used in magnetoencephalography prototypes which are devices for recording the cerebral magnetic field: [1], [2], [3].

These sensors are physically independent of one another and can be positioned as close as possible to the scalp of the patient. The interest is in optimizing the signal-to-noise ratio since the magnetic field decreases with distance. That also makes it possible to maintain a relative position of the sensors with respect to the head which is fixed.

Another means of enhancing the measured signal quality is to have a reference sensor placed at a distance from the cerebral signal measurement sensors: [4].

In the MEG helmets based on SQUID (acronym for "Superconducting QUantum Interference Device") sensors, this approach has already been used.

However, because of the configuration of the equipment, conditioned by the use of cryogenic fluid (liquid helium), the matrix of SQUID sensors measuring the cerebral signal was situated within a rigid helmet and reference sensors were placed, for example, at the top of the liquid helium vessel. Reference will be able to be made to the MEG equipment marketed under the marketing designation CTF.

The relative distances and positions of the reference sensor or sensors with respect to the SQUID measurement sensors were therefore defined in advance and definitively fixed.

Now, in the case of an MEG helmet with OPM sensors for the measurement, the latter are borne directly on the head of the patient. The use of a reference sensor therefore necessitates being able to position it at a distance from the measurement OPM sensors while ensuring that it is held fixed with respect to the latter, regardless of the movements of the head of the patient.

The patent JP2020151023 describes and claims a support mounted on the head, a fixing of the sensor and a sensor of OPM type placed facing the region of the cortex defined by the Broadman area.

For its part, the patent CN105147289 describes and claims an MEG helmet made of elastic material fixed to the head by a chin rest.

The patent application WO2020/084194A1 claims a rigid helmet system, that can be adapted to different head sizes and that makes it possible to position OPMs in right and left temporal regions, above the ears of the user, to record cerebral responses to an auditory stimulus.

There is a need to enhance the systems for fixing reference sensors to the MEG helmets, notably those of the existing systems, as mentioned hereinabove, when the measurement sensors are OPM sensors.

The general aim of the invention is then to at least partly address this need.

SUMMARY OF THE INVENTION

To do this, the subject of the invention is first of all a system for positioning and maintaining the position of a reference sensor on a magnetoencephalography MEG helmet, comprising:

an arch comprising:
at least one fixing branch for fixing the arch to an MEG helmet,
a support plate to which the branch is fixed,
a sensor support post fixed to the support plate of the arch;
a locking piece for fixing the reference sensor to the post according to at least one position defining the position with respect to an MEG helmet.

According to an advantageous embodiment, the arch comprises two branches arranged symmetrically to one another with respect to the support plate.

Preferably, the post is a hollow post extending on a longitudinal axis (X) in which the reference sensor can be inserted according to several longitudinal positions.

According to a variant embodiment, the hollow of the post comprises a plurality of wedging slits, spaced apart longitudinally, each forming a support for a positioning wedge for positioning the sensor according to a longitudinal position.

The locking piece is preferably a locking ring to be tightened around the hollow post.

According to an advantageous variant embodiment, the arch comprises shutes for positioning cables of OPM sensors fixed to the MEG helmet.

Each fixing branch preferably comprises, at its free end, a plate to be screwed to the MEG helmet by means of a tightening thumbwheel.

Advantageously, the arch, the post and the locking piece are made of plastic material, preferably of polyamide.

The invention relates finally to an assembly comprising a magnetoencephalography MEG helmet to which is fixed the system for positioning and maintaining the position described previously.

According to an advantageous variant, the helmet comprises at least one anchor point to which the fixing branch is fixed by means of a tightening thumbwheel, the anchor point being an inclined flat provided with a drilled and tapped hole into which the tightening thumbwheel is screwed.

Thus, the invention consists essentially of a system for positioning and maintaining the position of a reference sensor, that makes it possible to position this reference sensor at different distances from a magnetoencephalography helmet supporting OPM sensors for measuring the cerebral signal.

This system essentially comprises an arch that is intended to be fixed at at least one point, even at two points, to the MEG helmet, and a post that is fixed, preferably at the top, of the flexible helmet in which the reference sensor is placed.

This post preferably incorporates wedging slits defining several predefined positions to make it possible to position the reference sensor at different distances from the OPM sensors measuring the cerebral signal.

The locking piece makes it possible to maintain the position of the reference sensor.

Preferably, the fixing of the system according to the invention is done directly on the flexible helmet bearing the measurement OPM sensors thus allowing the reference sensor to keep a distance and a fixed relative position with respect to the measurement OPM sensors, regardless of the movements of the head of the patient.

Other advantages and features will emerge more clearly on reading the detailed description, given in an illustrative and nonlimiting manner, with reference to the following figures.

DETAILED DESCRIPTION

Figure 1:
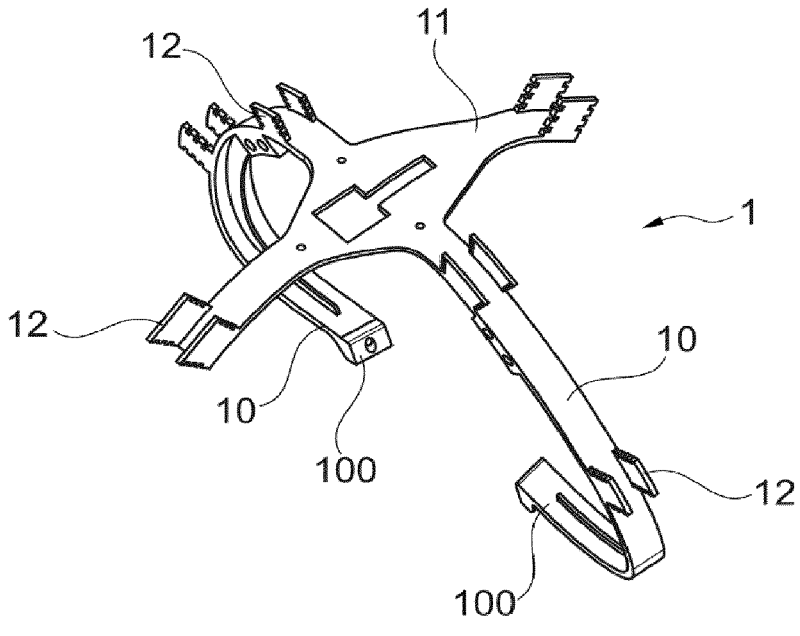
FIG. 1 is a perspective view of an arch of a positioning system according to the invention.
Figure 2:
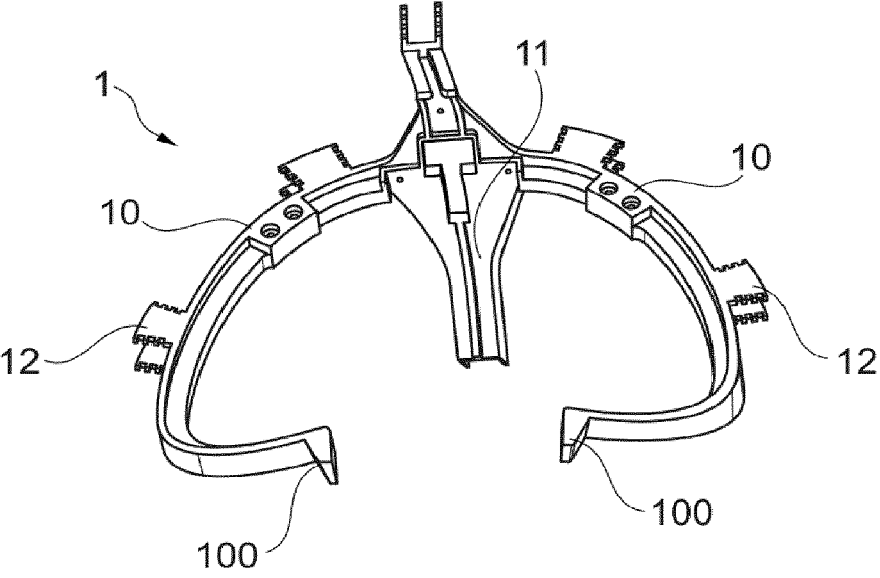
FIG. 2 is another perspective view of the arch according to FIG. 1.

FIGS. 1 and 2 show an arch 10 of the system for positioning and maintaining the position of the reference sensor according to the invention.

The arch 10 is designed as to be flexible enough to be able to adapt to different head morphologies: based on the morphology, the arch must be able more or less to bend and be sufficiently rigid to allow a sensor support post 2 to be held well as detailed hereinbelow.

The arch 10 can be produced in a plastic material, typically in PLA.

This arch 10 comprises two fixing branches 10 arranged symmetrically on either side of a support plate 11.

Each branch 10 is preferably a branch arranged laterally with respect to the support plate 11.

Each branch 10 has a free end 100 that is drilled for fixing to an anchor point 3.

Figure 3:
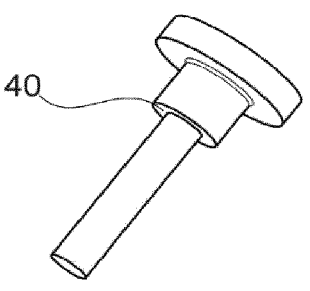
FIG. 3 is a view of a fixing thumbwheel of the system with an MEG helmet according to the invention.

Each free end 100 can be fixed by means of a tightening thumbwheel 40 shown in FIG. 3 on an anchor point provided on an MEG helmet.

Figure 4:
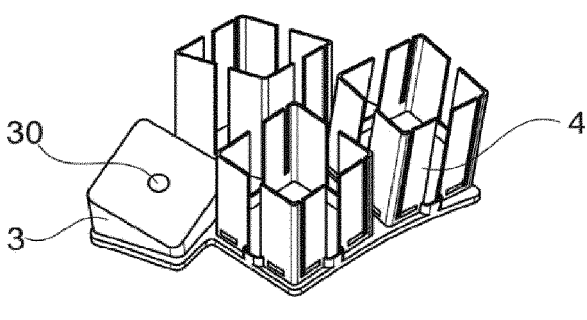
FIG. 4 is a perspective view showing a fixing piece of an MEG helmet for fixing of the arch.

FIG. 4 shows an example of anchor point 3 as it can be arranged in an MEG helmet.

The anchor point 3 is an inclined flat provided with a drilled and tapped hole 30 at its center in which the tightening thumbwheel is screwed. An anchor point 3 is preferably arranged in the MEG helmet, on either side of the head, behind the ears and facing the zones of the cranium called mastoids.

The inclination of the flat 3 is designed to adapt to the fixing zone situated at each end 100 of the lateral branches 10 of the arch.

As illustrated in FIG. 4, each anchor point 3 forms part of a block of a number of three support studs 4 for OPM measurement sensors of the MEG helmet.

The arch 10 also comprises chutes 12 on each of its branches 10 and preferably on the support plate 11. These chutes 12 make it possible to position the cables of the measurement OPM sensors situated on the head of the patient, in order to keep them stable and avoid any pulling effect on the OPM measurement sensors. This makes it possible to guarantee a low measurement noise level.

Figure 5:
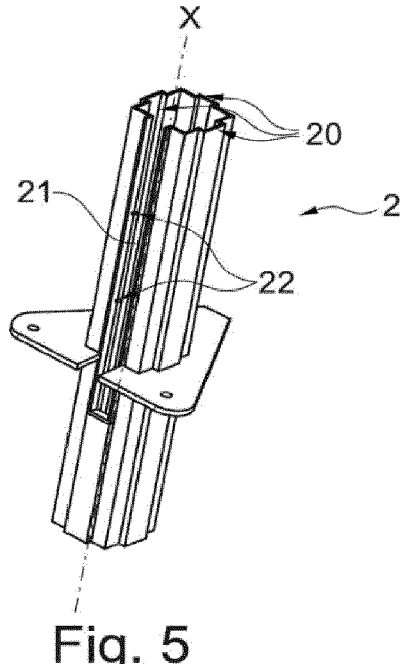
FIG. 5 is a perspective view of a post of the positioning system according to the invention.

FIG. 5 shows a hollow post 2 for supporting the reference sensor.

This post 2 is fixed to the support plate 11 of the arch 10 via a fixing plate 13.

This post 2 is of square section. It has an opening on one face and the other three faces are grooved at their center, in order to distance the material from certain sensitive elements of the reference sensor.

The post 2 comprises a central hollowed part 21. This hollowed part extends preferably only over a substantial part of its height, that is to say not to the bottom of the post 2 so as to have a rigid stable fixing on a probe location provided for this purpose on an MEG helmet. This hollowed part 21 makes it possible to insert the reference sensor. Wedging slits 22 are arranged along the post at different longitudinal positions. These slits 22 make it possible to position the reference sensor longitudinally at several different distances from the measurement OPM sensors placed on the scalp of the patient.

Figure 6:
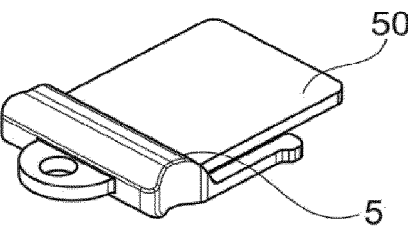
FIG. 6 is a perspective view of a locking ring of the reference sensor.

A wedge piece 5 shown in FIG. 6 makes it possible to set the chosen height by being inserted into the post 2 at one or other of the slits 22 for a given position.

Figure 7:
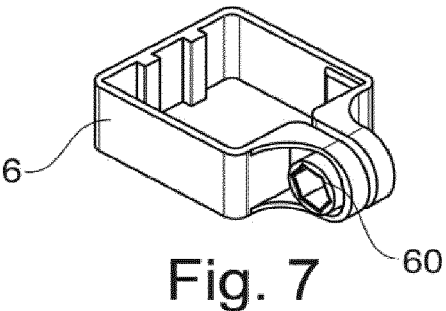
FIG. 7 is a perspective view of a wedging piece in the longitudinal positioning of the reference sensor in the post.

A locking ring 6 shown in FIG. 7 is fixed around the post 2 to lock and maintain the reference sensor in fixed position with respect to the measurement OPM sensors, and do so regardless of the head movements of the patient.

More specifically, the wedge piece 5 is composed of a tongue 50 which is inserted into one of the two slits 22 of the post 2 at the chosen longitudinal position.

A reference sensor is slid into the post 2 and then rests on this wedge piece 5.

The locking ring 6 is then positioned facing the top part of the reference sensor, around the post 2, and it is tightened using a screw.

The positioning system according to the invention which has just been described is fixed to an MEG helmet 7 that can accommodate an OPM sensor for measuring the cerebral signal, as follows.

The base of the post 2 is fixed to a support stud, of the type of that referenced in FIG. 4, at the top of the MEG helmet.

The arch 1 is fixed at two lateral anchor points to the MEG helmet.

Figure 8:
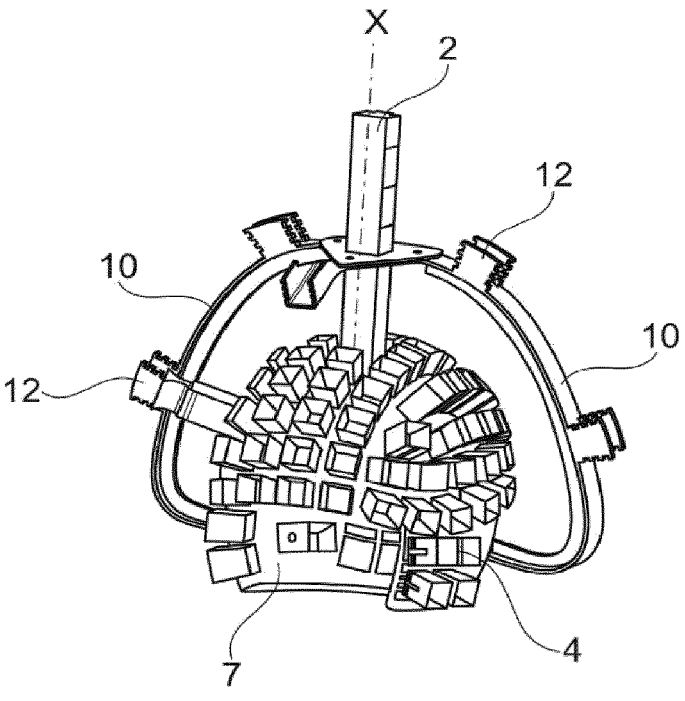
FIG. 8 is a perspective view of the positioning system according to the invention fixed to the MEG helmet.
Figure 9:
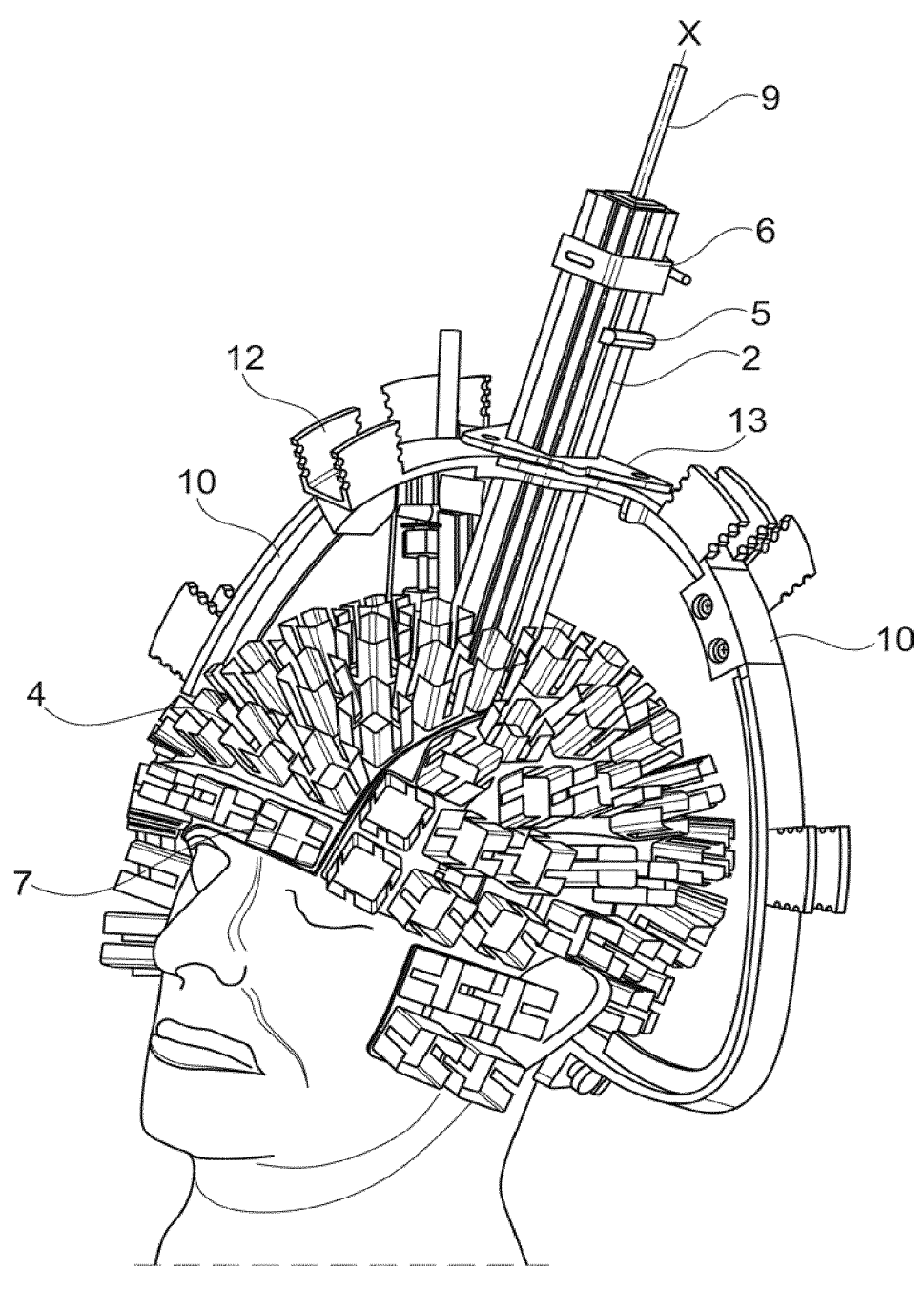
FIG. 9 is another perspective view of the positioning system according to the invention fixed to the MEG helmet, with a reference sensor positioned and fixed.

FIGS. 8 and 9 show an MEG helmet with its OPM sensor support studs 4 and the system for positioning and maintaining the position of a reference sensor 8 which is fixed to it.

In a concrete embodiment, the system for positioning and maintaining the position of the reference sensor described has been designed to adapt to an MEG flexible helmet 7 comprising a number of 97 support studs 4 for the OPM sensors for measuring the cerebral signal.

In FIG. 9, a reference sensor 8 linked to its cable 9 is inserted into the post 2 and is locked therein and maintained in fixed position by means of the ring 6 tightened by means of a tightening thumbwheel 61 screwed into the tightening eyelets 60.

Figure 10:
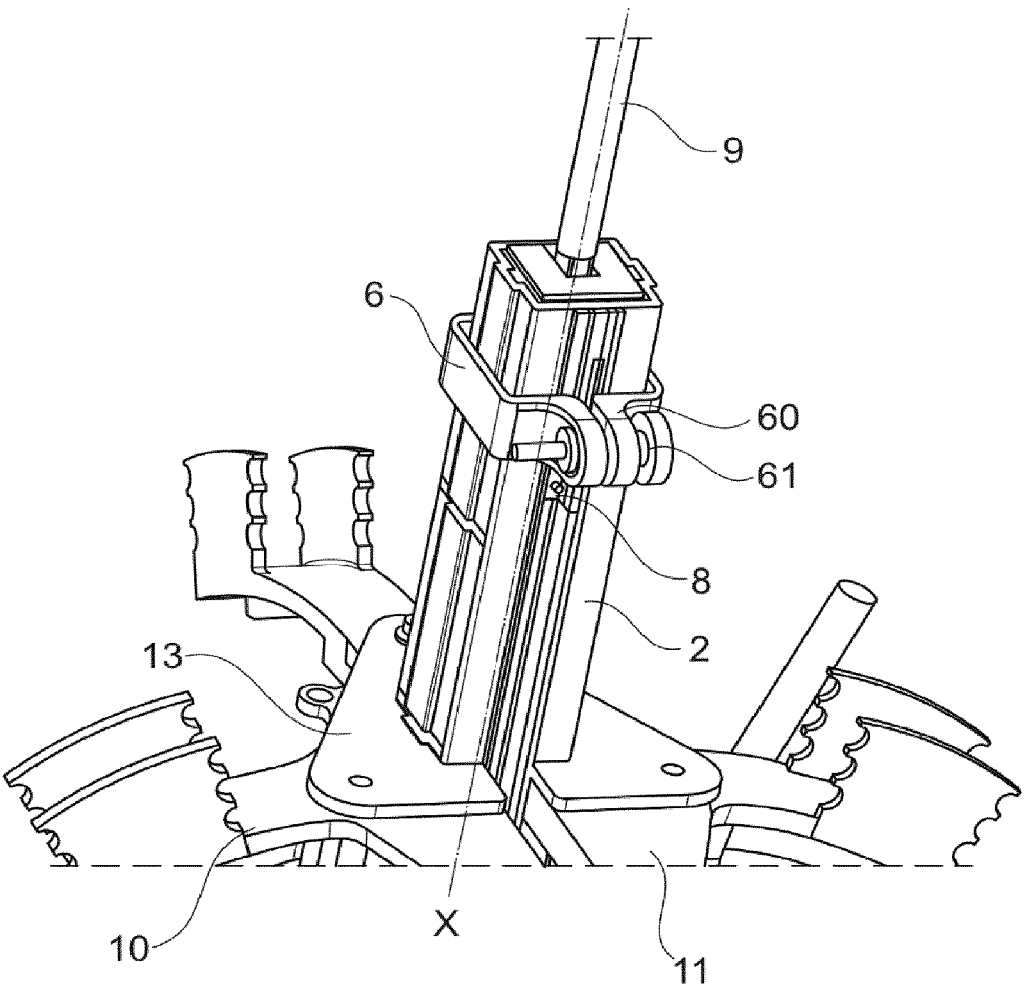
FIG. 10 is a perspective view of the positioning system according to the invention with a reference sensor fixed by means of a tightening ring on the support post.

FIG. 10 reprises FIG. 9, additionally showing the wedging piece 5 which, inserted into the wedging slits 22, supports and maintains the reference sensor 8, inserted into the post 2, in a given longitudinal position.

The invention is not limited to the examples which have just been described; it is notably possible to combine with one another the features of the examples illustrated in variants that are not illustrated.

Other variants and enhancements can be envisaged without in any way departing from the framework of the invention.

In the example illustrated in FIG. 8, the support post 2 is fixed to the support plate 11 of the arch 1 in such a way that it is substantially positioned at the top of the head of a person on which the magnetoencephalography is to be performed. Obviously, other fixing positions around the cranium of a person can be envisaged.

In the example illustrated in FIG. 4, the anchor points 3 are provided at the mastoids. In fetal and magnetocardiography (MCG) MEG variations, it is possible to envisage positioning these anchor points 3 respectively at the iliac crests (fetal MEG) or acromions (MCG).

LIST OF THE REFERENCES CITED

[1]: Boto et al., "*Moving magnetoencephalography towards real-world applications with a wearable system*". Nature. 2018 Mar. 29; 555(7698):657-661 DOI: 10.1038/nature26147.
[2]: Hill et al., "*Multi-Channel Whole Head OPM-MEG*": Helmet design and a comparison with a conventional system NeuroImage Vol 219, 1 Oct. 2020, 116995https://doi.org/10.1016/j.neuroimage.2020.116995.
[3]: Borna et al, "*Non-Invasive Functional-Brain-Imaging with an OPM-based Magnetoencephalography System*" PLoS ONE 15(1). 2020 https://doi.org/10.1371/journal.pone.0227684.
[4]: A. A. FifeJ. Vrba, S. E. Robinson[ . . . ] W. Sutherling. "*Synthetic gradiometer systems for MEG*." July 1999 IEEE Transactions on Applied Superconductivity.

6

The invention claimed is:

1. A system for positioning and maintaining a position of a reference sensor on a magnetoencephalography (MEG) helmet, the system comprising:
an arch including at least one fixing branch to fix the arch to the MEG helmet, and a support plate to which each fixing branch of the at least one fixing branch is fixed,
a sensor support post, different from the at least one fixing branch, fixed to the support plate of the arch, the sensor support post being fixed at a top of the MEG helmet and extending through the arch; and
a locking piece to fix the reference sensor to the sensor support post in at least one position defining the position with respect to the MEG helmet.

2. The system as claimed in claim 1, wherein the arch comprises two fixing branches arranged symmetrically with respect to one another with respect to the support plate.

3. The system as claimed in claim 1, wherein the sensor support post is a hollow post extending on a longitudinal axis in which the reference sensor can be inserted according to several longitudinal positions.

4. The system as claimed in claim 3, wherein the hollow post comprises a plurality of wedging slits, spaced apart longitudinally, each forming a support for a positioning wedge for positioning the reference sensor according to a longitudinal position.

5. The system as claimed in claim 3, wherein the locking piece is a locking ring to be tightened around the hollow post.

6. The system as claimed in claim 1, wherein the arch comprises shutes to position cables of OPM sensors fixed to the MEG helmet.

7. The system as claimed in claim 1, wherein each fixing branch, of the at least one fixing branch, comprises, at a free end thereof, a plate to be screwed onto the MEG helmet by a tightening thumbwheel.

8. The system as claimed in claim 1, wherein the arch, the sensor support post, and the locking piece are made of plastic material.

9. An assembly, comprising:
the MEG helmet; and
the system for positioning and maintaining the position as claimed in claim 1, the system being fixed to the MEG helmet.

10. The assembly as claimed in claim 9, wherein the MEG helmet further comprises at least one anchor point to which the at least one fixing branch is fixed by a tightening thumbwheel, the anchor point being an inclined flat provided with a drilled and tapped hole into which the tightening thumbwheel is screwed.

* * * * *